(12) United States Patent
Samulski et al.

(10) Patent No.: US 6,548,286 B1
(45) Date of Patent: Apr. 15, 2003

(54) METHODS FOR INCREASING THE EFFICIENCY OF RECOMBINANT AAV PRODUCT

(75) Inventors: Richard Jude Samulski, Chapel Hill, NC (US); Xiao Xiao, Wexford, PA (US); Richard Snyder, Oakland, CA (US)

(73) Assignees: Cell Genesys, Inc., Foster City, CA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/060,102

(22) Filed: Apr. 14, 1998

(Under 37 CFR 1.47)

Related U.S. Application Data

(60) Provisional application No. 60/043,547, filed on Apr. 14, 1997.

(51) Int. Cl.$^7$ .............................. C12N 7/01; C12N 5/10
(52) U.S. Cl. .................................... 435/235.1; 435/369
(58) Field of Search .............................. 435/235.1, 325, 435/369

(56) References Cited

U.S. PATENT DOCUMENTS

| | | | |
|---|---|---|---|
| 5,139,941 A | 8/1992 | Muzyczka et al. | |
| 5,436,146 A | 7/1995 | Shenk et al. | |
| 5,622,856 A | 4/1997 | Natsoulis | |
| 5,753,500 A | 5/1998 | Shenk et al. | |
| 5,837,484 A | * 11/1998 | Trempe et al. | 435/69.1 |
| 6,001,650 A | 12/1999 | Colosi | |
| 6,027,931 A | 2/2000 | Natsoulis et al. | |
| 6,037,177 A | * 3/2000 | Snyder | 435/455 |
| 6,086,913 A | * 7/2000 | Tam et al. | 424/450 |
| 6,365,403 B1 | 4/2002 | Natsoulis et al. | |

FOREIGN PATENT DOCUMENTS

| | | |
|---|---|---|
| WO | WO 95/14771 | 6/1995 |
| WO | WO 97/09441 | 3/1997 |

OTHER PUBLICATIONS

Antoni et al., 1991, "Adeno–Associated Virus Rep Protein Inhibits Human Immunodeficiency Virus Type 1 Production in Human Cells", J. Virol. 65:396–404.

Chejanovsky and Carter, 1989, "Mutagenesis of an AUG Codon in the Adeno–Associated Virus rep Gene: Effects on Viral DNA Replication", Virol. 173:120–128.

Clark et al., 1995, "Cell Lines for the Production of Recombinant Adeno–Associated Virus", Human Gene Ther. 6:1329–1341.

Flotte and Carter, 1995, "Adeno–Associated Virus Vectors for Gene Therapy", Gene Ther. 2:357–362.

Flotte et al., 1995, "An Improved System for Packaging Recombinant Adeno–Associated Virus Vectors Capable of In Vivo Transduction", Gene Ther. 2:29–37.

Giraud et al., 1994, "Site–Specific Integration by Adeno–Associated Virus Is Directed by a Cellular DNA Sequence", Proc. Natl. Acad. Sci USA 91:1003*–10043.

Guarino and Summers, 1986, "Interspersed Homologous DNA of Autographa californica Nuclear Polyhedrosis Virus Enhances Delayed–Early Gene Expression", J. Virol. 60:215–223.

Heilbronn et al., 1990, "The Adeno–Associated Virus rep Gene Suppresses Herpes Simplex Virus–Induced DNA Amplification", J. Virol. 64:3012–3018.

Hermonat, 1994, "Down–Regulation of the Human c–fos and c–myc Proto–Oncogene Promoters by Adeno–Associated Virus Rep78", Cancer Lett.81:129–136.

Hermonat et al., 1984, Genetics of adenso–associated virus: isolation and preliminary characterization of adeno–associated virus type 2 mutants. J Virol. 51(2):329–39.

Horer et al., 1995, "Mutational Analysis of Adeno–Associated Virus Rep Protein–Mediated Inhibition of Heterologoous and Homologous Promoters", J. Virol. 69:5485–5496.

Inoue et al., 1998, Packaging cells based on inducible gene amplification for the production of adeno–associated virus vectors, J Virol.72(9):7024–31.

Koeberl et al., 1997, "Persistent Expression of Human Clotting Factor IX from Mouse Liver after Intravenous Injection of Adeno–Assocated Virus Vectors", Proc. Natl. Acad. Sci. USA 94:1426–1431.

Kotin, 1994, Prospects for the use of adeno–associated virus as a vector for human gene therapy. Hum Gene Ther. 5(7):793–801.

(List continued on next page.)

Primary Examiner—James Ketter
(74) Attorney, Agent, or Firm—Pennie & Edmonds LLP; Linda R. Judge; Cell Genesys, Inc.

(57) ABSTRACT

The present invention relates to methods and compositions for increasing the production of high titre stocks of recombinant AAV (rAAV) through regulation of expression of the AAV REP and CAP proteins. The methods and compositions of the invention are based on the observation that the low level expression of the AAV REP protein increases the production of AAV viral capsid protein and efficiency of packaging resulting in production of higher titre recombinant viral stocks. The invention encompasses recombinant AAV vectors that direct the expression of AAV REP and CAP proteins and the use of such vectors for the production of novel stable cell lines capable of generating high titre rAAV vectors. The invention provides methods for regulating the expression of the AAV REP gene at the transcriptional and post-translational level. The methods and compositions of the invention can be used to produce high titre stocks of rAAV which can be used in gene therapy for the purpose of transferring genetic information into appropriate host cells for the management and correction of human diseases including inherited and acquired disorders.

14 Claims, 5 Drawing Sheets

OTHER PUBLICATIONS

Figure 1:
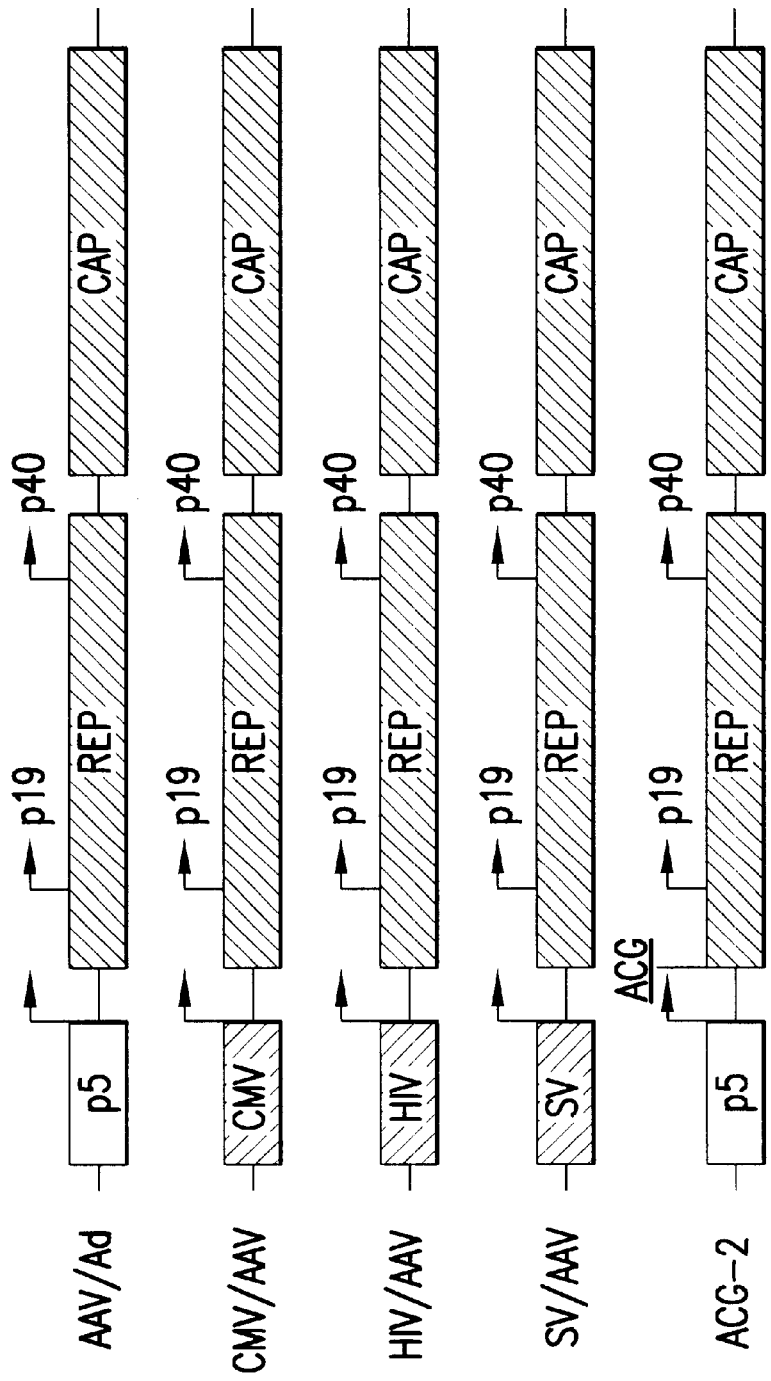

Kozak, 1986, "Point Mutations Define a Sequence Flanking the AUG Initiator Codon that Modulates Translations by Eukaryotic Ribosomes", Cell 44:283–292.

Labow et al., 1987, "Adeno–Associated Virus Gene Expression Inhibits Cellular Transformation by Heterologous Genes", Mol. Cell. Biol. 7:1320–1325.

Lebkowski et al., 1988, "Adeno–Associated Virus: A Vector System for Efficient Introduction and Integration of DNA into a Variety of Mammalian Cell Types", Mol. Cell. Biol. 8:3988–3996.

Li, et al., 1997, Role for highly regulated rep gene expression in adeno–associated virus vector production. J Virol. 71(7):5236–43.

McCarty et al., 1991, "Sequences Required for Coordinate Induction fo Adeno–Associated Virus p19 and p40 Promoters by Rep Protein", J. Virol. 65:2936–2945.

Muzyczka, 1991, "In Vitro Replication of Adeno–Associated Virus DNA", Virol. 2:281–290.

Muzyczka, 1992, "Use of Adeno–Associated Virus as a General Transduction Vector for Mammalian Cells", Curr. Top. Microbiol. Immunol. 158:97–129.

Pereira, et al., 1997, "The adeno–associated virus (AAV) Rep protein acts as both a repressor and an activator to regulate AAV transcription during a productive infection." J Virol. 71(2):1079–88.

Samulski et al., 1989, "Helper–Free Stocks of Recombinant Adeno–Associated Viruses: Normal Integration Does Not Require Viral Gene Expression", J. Virol. 63:3822–3828.

Samulski et al., 1991, "Targeted Integration of Adeno–Associated Virus (AAV) into Human Chromosome 19", EMBO J. 10:3941–3950.

Senapahty P and Carter BJ, 1984, Molecular cloning of adeno–assocated virus variant genomes and generation of infectious virus by recombination in mammalian cells J. Biol Chem. 259(7):4661–6.

Tamayose et al., 1996, "A new strategy for large–scale preparation of high–titer recombinant adeno–associated virus vectors by using packaging cell lines and sulfonated cellulose column chromatography." Hum Gene Ther. 7(4):507–13.

Tratschin et al., 1986, "Negative and Positive in trans of Gene Expression from Adeno–Associated Virus Vectors on Mammalian Cells by a Viral rep Gene Product", Mol. Cell. Biol. 6:2884–2894.

Vincent, 1997, "Analysis of recombinant adeno–associated virus packaging and requirments for rep and cap gene products." J Virol. 71(3):1897–905.

Weitzman et al., 1994, "Adeno–associated virus (AAV) Rep proteins mediate complex formation between AAV DNA and its integration site in human DNA." Proc Natl Acad Sci U S A. 91(13):5808–12.

Yang et al., 1994, "Characterization of cell lines that inducibly express the adeno–associated virus Rep proteins." J Virol.;68(8):4847–56.

* cited by examiner

METHODS FOR INCREASING THE EFFICIENCY OF RECOMBINANT AAV PRODUCT

This application claims benefit of provisional application 60/043,547 filed Apr. 14, 1997.

The invention was made with government support under Grant #PO1 HL51818-01, awarded by the National Institutes of Health. The government has certain rights in this invention.

1. INTRODUCTION

The present invention relates to methods and compositions for increasing the production of high titre stocks of recombinant AAV (rAAV) through regulation of expression of the AAV REP proteins. The methods and compositions of the invention are based on the observation that low level expression of the AAV REP protein increases the efficiency of rAAV DNA replication and the production of AAV viral capsid protein resulting in production of higher titre recombinant viral stocks. The invention encompasses methods and compositions for controlling the level of REP expression at the transcriptional or translational level. Additionally, the invention provides methods for regulating the biological activity and/or stability of the REP proteins at the post-translational level. The methods and compositions of the invention can be used to produce high titre stocks of rAAV which can be used in gene therapy for the purpose of transferring genetic information into appropriate host cells for the management and correction of human diseases including inherited and aquired disorders.

2. BACKGROUND OF THE INVENTION

2.1. GENE THERAPY

Gene therapy is generally understood to refer to techniques designed to deliver functionally active therapeutic genes into targeted cells. Such therapeutic genes may encode proteins that complement genetic deficiencies, cytokines, cell surface membrane proteins or any protein that functions to regulate cell growth and/or differentiation. Such proteins may function intracellularly, for example, by regulating a signalling pathway or transcriptional pathway. Alternatively, the proteins may be secreted by the cell and exert their effect extracellularly.

Initial efforts toward somatic gene therapy have relied on indirect means of introducing genes into tissues, e.g., target cells are removed from the body, transfected or infected with vectors carrying recombinant genes, and reimplanted into the body. These types of techniques are generally referred to as in vitro treatment protocols.

In addition, recombinant replication-defective viral vectors have been used to infect cells both in vitro and in vivo. Perhaps the most widely studied viral vectors for use in gene therapy have been the retroviral vectors. The major disadvantages-associated with the use of retroviral vectors include the inability of many viral vectors to infect non-dividing cells, problems associated with insertional mutagenesis and potential helper virus production. Recently, attention has turned to the use of other types of recombinant viral vectors such as adenovirus and adeno-associated virus based vectors, that may be used to deliver genes of interest to cells.

In particular, recombinant adeno-associated virus has many features of interest in the field of gene therapy. The vectors are based on a defective, nonpathogenic human parvovirus that can infect both dividing and non-dividing cells without a marked tropism. In addition, the viral genome can stably integrate within the host genome, facilitating long term gene transfer.

2.2. AAV VIRAL VECTORS

The AAV genome is composed of a linear single stranded DNA molecule of 4680 nucleotides which contains major open reading frames coding for the Rep (replication) and Cap (capsid) proteins. Flanking the AAV coding regions are two 145 nucleotide inverted terminal (ITR) repeat sequences that contain palindromic sequences that can fold over to form hairpin structures that function as primers during initiation of DNA replication. In addition, the ITR sequences are needed for viral integration, rescue from the host genome and encapsidation of viral nucleic acid into mature virions (Muzyczka, N., 1992, Current Topics in Microbiology & Immunology. 158, 97–129).

AAV can assume two pathways upon infection into the host cell depending on whether helper virus is present. In the presence of helper virus, AAV will enter the lytic cycle whereby the viral genome is transcribed, replicated, and encapsidated into newly formed viral particles. In the absence of helper virus function, the AAV genome will integrate as a provirus into a specific region of the host cell genome through recombination between the AAV termini and host cell sequences (Cheung, A. et al., 1980, J. Virol. 33:739–748; Berns, K. I. et al., 1982, in Virus Persistence, eds. Mahey, B. W. J., et al. (Cambridge Univ. Press, Cambridge), pp. 249–265).

The use of AAV as a vehicle for the transfer of genetic information has been facilitated by the discovery that when a plasmid containing an intact AAV genome is transfected into a host cell the recombinant AAV vector will integrate into the host cell genome and remain as a provirus until the host cell subsequently becomes infected with a helper virus. Upon infection of the host cell with helper virus, the AAV is rescued out from the plasmid vector and enters the lytic cycle leading to production of mature virions.

The production of rAAV particles, utilizes a vector containing a transgene flanked by the inverted terminal repeats (ITR), which are the sole AAV cis sequences required for DNA replication, packaging and integration. To produce rAAV particles, the AAV (Rep) and capsid (Cap) gene products are normally provided in trans from a different template, usually a helper plasmid.

The three viral coat proteins, VP1, VP2, and VP3 which are required for virion expression are derived from mRNA initiated at the p40 promoter, while the four overlapping non-structural Rep proteins are essential for AAV DNA replication. Rep78 and 68 are expressed from unspliced and spliced transcripts initiating at the p5 promoter, while Rep52 and Rep40 are similarly produced from transcripts initiating at the p19 promoter. Although Rep52/40 have been implicated in AAV single stranded DNA formation (Chejanovsky et al., 1989, Virology 173:120–128) and gene regulation, Rep appear to display all enzyme functions essential for AAV DNA replication, (ITR binding, DNA helicase, and DNA site-specific nicking activity), (Muzyczka, N., 1991, Seminars in Virology 2:281–290). In addition to these functions, Rep both positively and negatively regulate AAV promoters (Labow et al., 1986, Journal of Virology 60:215–258; Pereira et al., 1997, J. Virol, In Press; Tratschin et al., 1986, Mol. Cell Biol. 6:2884–2894) and repress numerous heterologous promoters (Antoni et al., 1991, Journal of Virology 65:396–404; Heilbronn et al., 1990, Journal of Virology 64:3012–3018; Hermonat, P. L., 1994, Cancer Letters 81:129–36; Horer, et al., 1995, Journal of Virology 69:5485–5496; Labow et al., 1987, Molecular & Cellular Biology 7:1320–1325).

Rep gene expression appears to be critical for all steps of the AAV life cycle, including a latent state which occurs in the absence of a helper virus (Berns, K. I., 1990, Virology, 2ed, vol. 2; Berns, K. I., 1996, B. N. Fields et al. ed.; Samulski et al., 1989, Journal of Virology 63:3822–3828). Recently, Rep have also been associated with AAV site-specific integration (Giraud et al., 1994, Proceedings of the National Academy of Sciences of the United States of America; Kotin et al., 1990, Proceedings of the National Academy of Sciences of the United States of America 87:221–2215; Samulski et al., 1991, EMBO Journal 10:3941–3950; Weitzmann et al., 1994, Proceedings of the National Academy of Sciences of the United States of America 91:5808–5812). Repression of viral gene expression by rep and host YY1 protein appears to be required for establishment and maintenance of the latent state (Labow et al., 1986, Journal of Virology 60:251–258; Laughlin et al., 1982, Journal of Virology 41:868–876; Periera et al., 1997, J. Virol In Press; Shi et al., 1991, Cell 67:377–388). Such repression may be necessary to avoid the demonstrated cytostatic effect on the host cell by Rep gene products (Yang et al., 1994, Journal of Virology 68:4847–4856). During a lytic infection, the AAV promoters, particularly p5, are transactivated by the adenovirus ElA proteins and YY1 (Lewis, et al., 1995, J. Virol. 69:1628–1636; Shi et al., 1991, Cell. 67:377–388). The p5 products then positively regulate the p19 and p40 promoters, resulting in abundant production of Rep 52/40 and viral capsid proteins (Pereira et al., 1997, J. Virol. In Press). Early effort to by-pass AAV rep gene regulation by substituting the p5 promoter with the SV40 early promoter failed (Labow et al., 1988, Journal of Virology 62:1705–1712). Instead of constitutive Rep expression, the heterologous promoter unexpectedly behaved in the same manner as the endogenous p5 promoter; repressed in the absence and activated in the presence of Ad (Labow et al., 1988, Journal of Virology 62:1750–1712). While these studies were the first to suggest rep repression as a mechanism for regulating heterologous promoters, these findings also implied that AAV p5 products may be a rate-limiting factor in AAV production (Labow et al., 1988, Journal of Virology 62:1705–1712). Further efforts in this area have suggested that overexpression of Rep may increase rAAV vector yields (Flotte et al., 1995, Gene Therapy 2:29:37).

An essential feature for use of rAAV as an efficient delivery system is the ability to produce recombinant stocks of virus. Although rAAV titres can approach wild type (wt) levels after multiple rounds of purification and concentration, the overall total yield is still substantially lower than that of wild type AAV. Therefore, methods that increase the ability to produce high titre rAAV viral stocks will facilitate the use of rAAV delivery systems in gene therapy.

3. SUMMARY OF THE INVENTION

The present invention provides methods and compositions for increasing the production of high titre stocks of recombinant AAV. The invention is based on the discovery that decreased expression of AAV REP proteins results in increased synthesis of viral capsid proteins and replication of viral DNA resulting in production of high titre recombinant viral stocks. Such recombinant AAV stocks may be used in gene therapy for the purpose of transferring genetic information into appropriate host cells for the management and correction of human disease including inherited and acquired disorders such as cancer and AIDS.

The invention encompasses methods for increasing the production of high titre stocks of recombinant AAV by regulating the expression levels and/or activity of the AAV REP proteins in a host cell. The invention further encompasses compositions such as recombinant helper plasmids that are genetically engineered to express low levels of biologically functional viral REP proteins. In such helper plasmids the expression of REP proteins may be regulated at the transcriptional, translational and/or post-translational level.

The expression of REP proteins may be regulated at the transcriptional level through the use of tightly controlled promoter systems that result in either low level, or inducible, expression of the REP gene. Such promoters can be genetically engineered into recombinant helper plasmids that are designed to express low levels of REP protein. Further, triple helix molecules can be utilized to reduce the level of REP gene expression. Such triple helix molecules can be designed to hybridize to the promoter region of the REP gene and thereby inhibit REP gene transcription.

Further, the invention encompasses the coding region of the REP genes which are genetically engineered to replace the initiator MET codon with a less efficiently translated initiator codon. The genes encoding the viral REP proteins of the present invention can also be genetically engineered to contain specific 5' nucleotide sequences to which translation repressor proteins bind. The binding of such repressor proteins to the 5' end of the REP mRNA molecules will result in inhibition of REP mRNA translation. Using such a system the level of REP protein can be controlled by regulating the level and/or activity of the translational repressor protein in the host cell.

Alternatively, the level of REP expression may also be controlled altering the stability of REP mRNA. For example, the half life of the REP mRNAs may be significantly decreased by genetically engineering nucleotide sequences rich in A and U nucleotides in the 3' untranslated region (UTR). Additionally, REP mRNAs containing recognition sites in their 3' UTR for specific endonucleases may be generated using recombinant DNA techniques.

The level of REP protein may be controlled by taking advantage of a translational process referred to as translational recoding. In such a process, a specific recording signal in the mRNA molecule causes the growing polypeptide chain occassionally to slip backward by one nucleotide on the ribosome as translation proceeds, causing the mRNA to be read in the incorrect reading frame.

The level of REP protein expressed in a host cell may further be reduced through the use of antisense and ribozyme molecules. Antisense approaches involve the design of oligonucleotides that bind to the complementary REP RNA and suppress translation of REP RNA. Ribozymes molecules may be designed that include one or more sequences complementary to REP RNA and which function to specifically and efficiently catalyses endonucleolytic cleavage of REP RNA sequences.

Finally, mutant forms of the REP proteins may be generated that have decreased activity and/or decreased protein stability. The activity of the REP proteins may be regulated through the use of temperature sensitive REP mutants. Alternatively, REP proteins which are less stable, i.e., REP proteins that possess a shorter half-life or REP proteins that are more susceptible to proteolytic cleavage, may be utilized as a means for decreasing the activity of the REP proteins.

The invention is demonstrated by way of examples, in which the overexpression of the REP gene was shown to inhibit rAAV DNA replication and CAP gene expression. In contrast, reduced production of AAV REP protein expression was sufficient for production of higher titres of recombinant virus.

4. BRIEF DESCRIPTION OF THE DRAWINGS

FIG. 1. Construction of AAV helper plasmids. Plasmids AAV/AD and ACG-2 contain the endogenous p5 promoter (depicted in open boxes), while plasmids CMV/AAV, HIV/AAV and SV/AAV contain the heterologous promoters (depicted in hatched boxes) replacing the original p5 promoter. All the constructs contain the same AAV coding sequences, i.e. the Rep and Cap genes diagrammed in shaded boxes, except that construct ACG-2 has an ATC to ACG mutation at the translation initiation codon of Rep.

Figure 2:
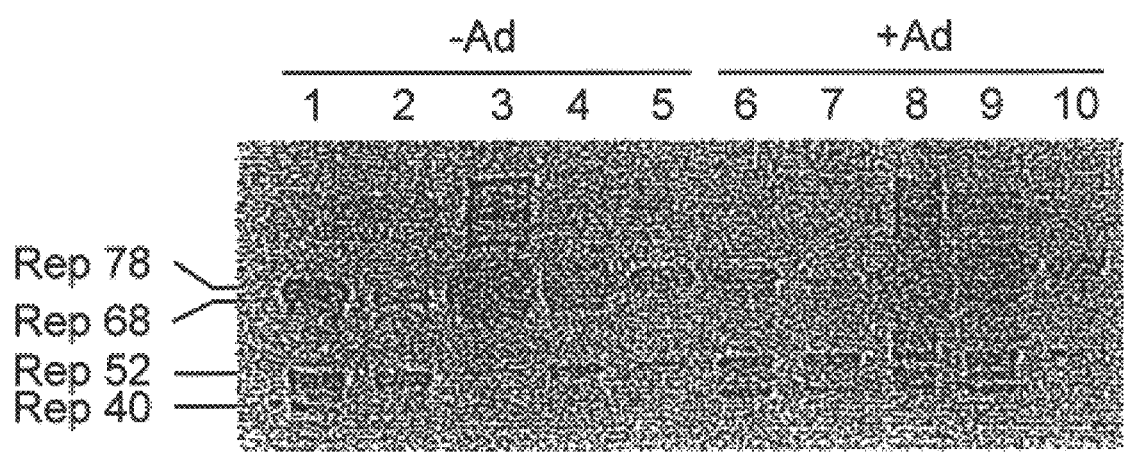

FIG. 2. Western analysis of Rep gene expression from various AAV helper plasmids. 293 cells were transfected with plasmid AAV/AD (lanes 1 & 6), ACG-2 (lanes 2 & 7), CMV/AAV (lanes 3 & 8), HIV/AAV (lanes 4 & 9) and SV/AAV (lanes 5 & 10) in the absence of Ad infection (lanes 1 through 5) or in the presence of Ad infection (lanes 6 through 10). Samples of cell lysates were separated by 10% PAGE. Western blot was performed with an anti-Rep monoclonal antibody, which recognizes all four Rep proteins (Hunter et al., 1992, J. Virology 66:317–324).

Figure 3:
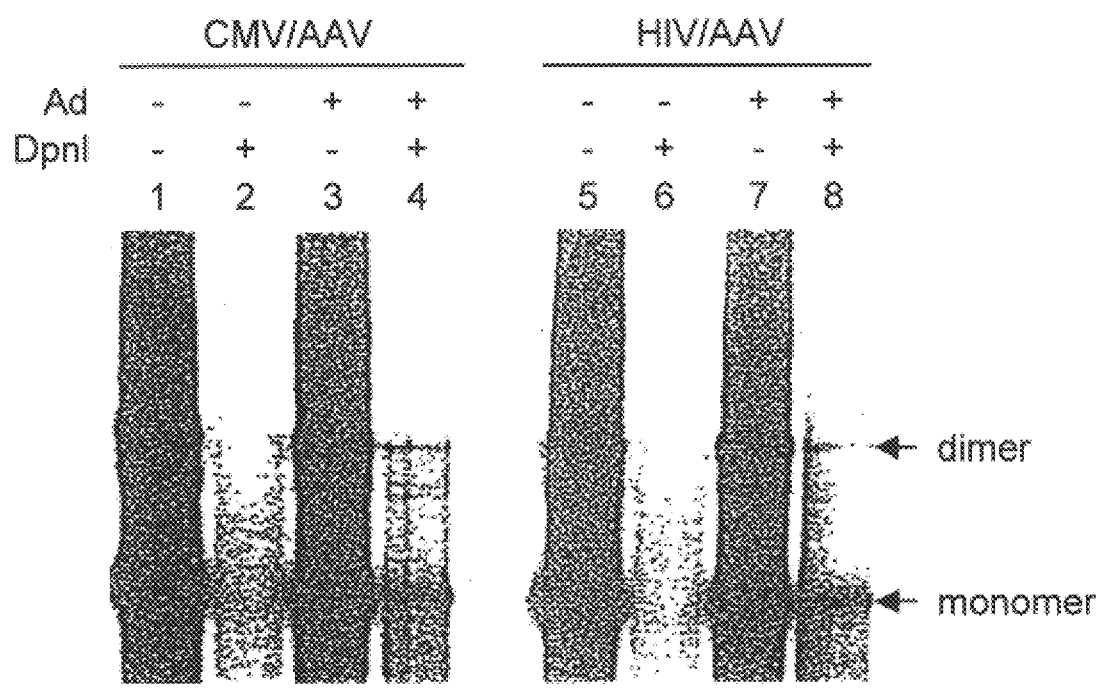

FIG. 3. Southern analysis of rAAV DNA replication. AAV vector plasmid pdx3l-LacZ were cotransfected into 293 cells with helper plasmids CVM/AAV (lanes 1 through 4) or HIV/AAV (lanes 5 through 8) in the absence of adenovirus infection (lanes 1 & 2, 5 & 6) or in the presence of adenovirus infection (lanes 3 & 4, 7 & 8). Low molecular weight DNA were recovered from the cells and separated on 1% agarose gel without prior DpnI digestion (lanes 1, 3, 5 & 7) or with DpnI digestion (lanes 2, 4, 6 & 8). Southern blot was performed-with a $^{32}P$ labeled LacZ probe (a 2.1 kb ClaI/NdeI fragment).

Figure 4:
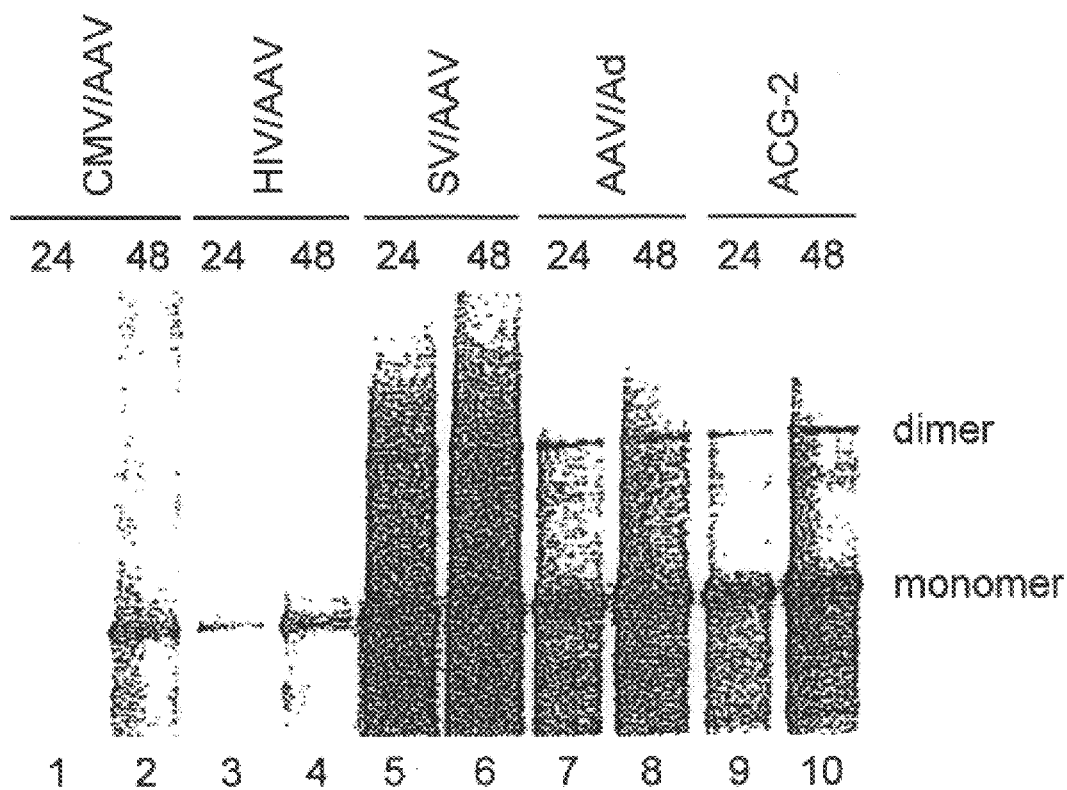

FIG. 4. Comparison of rAAV DNA replication in cells transfected with different helper plasmids. AAV vector plasmid pdx31-LacZ were cotransfected into 293 cells with helper plasmids CMV/AAV (lanes 1 & 2), HIV/AAV (lanes 3 & 4), SV/AAV (lanes 5 & 6), AAV/AD (lanes 7 & 8) and ACG-2 (lanes 9 & 01) in the presence of Ad infection. Low molecular weight DNA was recovered from the cells post transfection 24 hours (lanes 1, 3, 5, 7 and 9) or 48 hours (lanes 2, 4, 6, 8 and 10). Southern blot was performed with a 32p, labeled LacZ probe (a 2.1 kb Cla I/Nde I fragment).

Figure 5:
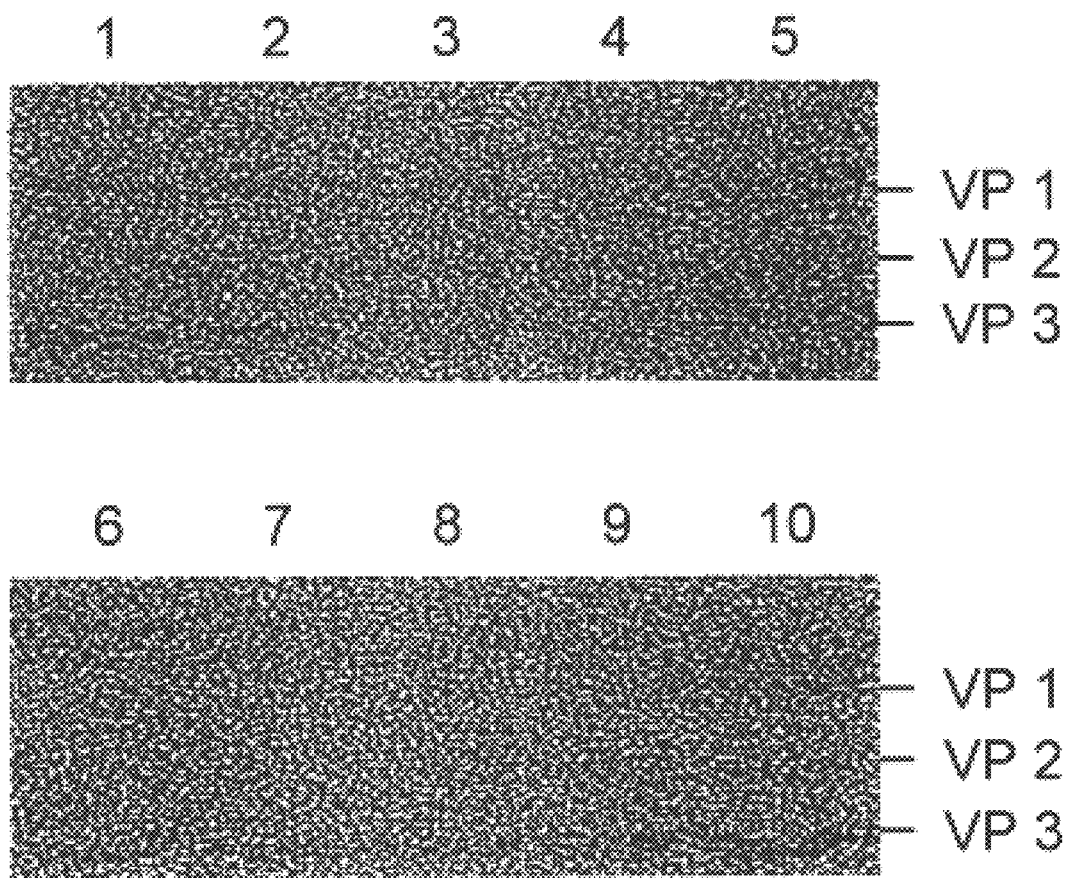

FIG. 5. Western analysis of Cap gene expression from different AAV helper plasmids. AAV vector plasmid pdx3l-LacZ were cotransfected into 293 cells with helper plasmids CMV/AAV (lanes 1 & 6), HIV/AAV (lanes 2 & 7), SV/AAV (lanes 3 & 8), AAV/AD (lanes 4 & 9) and ACG-2 (lanes 5 & 10) in the presence of Ad infection (lanes 1 through 5) or in the absence of Ad infection (lanes 6 through 10). Samples of cell lysates were separated by 10% PAGE. Western blot was performed with an anti-Cap polyclonal antibody which recognizes all three Cap proteins.

5. DETAILED DESCRIPTION OF THE INVENTION

The present invention relates to methods for increasing the production of high titre stocks of recombinant AAV (rAAV) through regulation of expression of the AAV REP proteins. To generate recombinant viral stocks, a recombinant vector containing a gene of interest and the cis-required AAV terminal repeat sequences is transfected into a host cell that is capable of providing helper virus function, and supplying in trans AAV REP and CAP proteins. The methods of the invention are based on the observation that low level in trans expression of the AAV REP proteins increases the efficiency of rAAV DNA replication and the production of AAV viral capsid protein resulting in production of higher titre recombinant viral stocks.

In particular, the invention described in the subsections below encompasses methods for regulating the level of REP protein expression. The expression of the REP proteins may be regulated at either the transcriptional or translational level. The invention relates to recombinant helper plasmids that are genetically engineered to express low levels of AAV viral REP protein. The expression of REP protein may be regulated at the level of transcription through the use of tightly controlled promoter systems. Alternatively, triple helix molecules may be utilized to interfere with the transcription of the REP genes.

The invention also encompasses the regulation of REP protein expression at the translational level through the use of antisense and ribozyme molecules. Further, the coding region of the REP genes may be genetically engineered to replace the initiator MET codon with a less efficiently translated initiator codon. In yet another embodiment of the invention, the level of REP protein may be regulated through genetic engineering of specific nucleotide sequences into the REP genes that function to decrease REP mRNA stability. Alternatively, nucleotide bind sites for translational repressor proteins may be genetically engineered into the REP gene sequences.

The present invention is based on the observation that when a series of AAV helper plasmids containing various strong heterologous promoters substituted for the AAV p5 promoter were transfected into human 293 cells, less efficient rAAV DNA replication and lower capsid protein synthesis was observed. In contrast, a novel construct which reduced REP expression, resulted in a 8 fold increase in rAAV yield. These observations indicate that unregulated overexpression of REP proteins adversely affects rAAV production arid suggest a role for highly regulated REP gene expression in optimal rAAV production.

5.1. RECOMBINANT EXPRESSION OF AAV REP PROTEIN

The present invention encompasses recombinant helper plasmids that are genetically engineered to provide in trans low level expression of viral REP protein. In accordance with the invention the open reading frame which encodes the AAV REP proteins may be engineered into expression vectors for highly regulated expression of the REP proteins. In order to express REP proteins, the nucleotide sequence coding for the REP proteins, or a functional equivalent, is inserted into an appropriate expression vector, i.e., a vector which contains the necessary elements for the highly regulated transcription and translation of the inserted REP coding sequences.

Methods which are well known to those skilled in the art can be used to construct expression vectors containing the REP protein coding sequences operatively associated with appropriate transcriptional/translational control signals for highly regulated expression of REP. These methods include in vitro recombinant DNA techniques, synthetic techniques, and in vivo recombination/genetic recombination. See, for example, the techniques and vectors described in Maniatis, et al., 1989, Molecular Cloning, A Laboratory Manual, Cold Spring Harbor Laboratory, N.Y. and Ausubel et al., 1989, Current Protocolsin Molecular Biology, Greene Publishing Associates & Wiley Interscience, N.Y.

The sequences of the AAV REP genes are reported in Srivastava, A., et al., 1983, J. Virol. 45:555–564; Muzyczka, N., 1992, Curr. Top. Micro Immunol. 158:97–129, and Ruffing, M., et al., 1992, J. Virol. 66:6922–6930, 1992. Sources for the AAV REP genes may include the mammalian virus serotypes AAV-1, AAV-2, AAV-3, AAV-4, and AAV-5, as well as bovine AAV and avian AAV. The invention contemplates, in addition to the REP DNA sequences disclosed therein, (1) any DNA sequence that encodes the same amino acid sequence for REP shown in Srivastava, A., et al., supra; Muzyczka, N., supra and Ruffing, M., et al. supra; (2) any DNA sequence that hybridizes to the complement of the coding sequences disclosed therein under highly stringent conditions, e.g., washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed therein under less stringent conditions, such as moderately stringent conditions, e.g., washing in 0.2×SSC/0.1% SDS at 42° C. (Ausubel et al., 1989, supra), yet which still encodes a functionally equivalent gene product.

Nucleic acids which encode derivatives (including fragments) and analogs of native REP proteins can also be used in the present invention, as long as such derivatives and analogs retain the ability to provide the functions required for AAV DNA replication. In particular, REP derivatives can be made by altering REP sequences by substitutions, additions, or deletions that provide for functionally active molecules that may have a altered phenotype. Furthermore, due to the degeneracy of nucleotide coding sequences, other DNA sequences which encode substantially the same or a functionally equivalent AAV REP amino acid sequence may be used in the practice of the methods of the invention. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the ampipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine.

In addition, nucleic acids which encode derivatives and analogs of native REP proteins with altered phenotypes may also be used in the present invention. In particular, alterations that decrease the biological activity of the AAV REP proteins and/or decrease the stability of the AAV REP proteins may be used. For example, nucleic acid molecules encoding temperature sensitive mutants of the REP protein may be genetically engineered into recombinant helper plasmids. Alternatively, nucleic acid molecules encoding REP proteins having a shorten half life, or REP proteins which are more susceptible to proteolytic cleavage may be engineered into recombinant helper plasmids.

A variety of host-expression vector systems may be utilized to express the AAV REP proteins. The expression systems that may be used for purposes of the invention include but are not limited to mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter;the vaccinia virus 7.5 K promoter). Promoters to express the REP proteins within a cell line may be drawn from those that are highly regulated within the host cell. Inducible gene regulation may be achieved using simple inducible promoter systems, including but not limited to, the metallothionine promoter (MT) and heat shock promoter, or by using the mouse mammary tumor virus promoter (MMTV) which is responsive to glucicorticoid stimulation. Alternatively, a more flexible though more complex inducible regulation system can be achieved through a "binary" gene approach. These binary regulation systems utilize a transactivator gene product to control expression of a second gene of interest. In addtion, repressor based binary systems may be used to regulate gene expression (Brown et al., 1987, Cell 48:555–566; Figge et al., 1988, Cell 49:603–612). For example, the tetR system utilizes the bacterial repressor tetR and insertion of tetR operator sequences in the promoter region of a gene of interest. Induction of gene expression in such a system involves the application of an inducer molecule that binds to and inactivates the repressor molecule resulting in activation of gene expression.

The REP coding region may be linked to any number of promoters in an expression vector that can be activated in the chosen cell line. Additionally, this cassette (REP genes and promoter) is carried by a vector that contains a selectable marker so that cells receiving the vector may be identified. Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Specific initiation signals are also required for sufficient translation of inserted protein coding sequences. These signals include the ATG initiation codon and adjacent sequences. These exogenous translational control signals and initiation sequences can be of a variety of origins, both natural and synthetic. For example, E. coli expression vectors will contain translational control sequences, such as an appropriately positioned ribosome binding site and initiation ATG.

Expression of the viral REP protein may be controlled at the level of translation by the replacement of the REP protein ATG start codon with the less efficient ACG codon resulting in a decrease in the production of REP protein. In a specific embodiment of the invention, a recombinant helper plasmid was constructed to contain an ATG to ACG mutation in the start codon of REP. When such a construct was utilized to generate rAAV stocks, the average yield of rAAV was increased by at least 8-fold when compared to plasmids expressing wild type levels of AAV REP protein.

In addition, the 5' end of the viral REP gene may be genetically engineered to contain specific nucleotide sequences to which translation repressor proteins bind (Melefors, 1993, Bioessays 15:85–90). Binding of the translation repressor protein to a mRNA molecule decreases the translation of the mRNA. Using such a system, the level of REP protein maybe controlled by regulating the level or activity of the translational repressor protein. Such sequences include, but are not limited to, sequences such as the iron-response element. The iron response element folds into a stem-loop structure that binds a translation repressor protein called aconitase which blocks the translation of any RNA sequence downstream. Aconitase is an iron-binding protein, and exposure of the cell to iron causes it to dissociate from the RNA, releasing the block to translation. Therefore, modification of the 5' end of the REP gene to include the iron responsive element provides a system for selectively and efficiently inducing the expression of the REP protein by exposing cells to iron.

The translation of REP mRNA may also be controlled taking advantage of a translational process referred to as translational recoding. In such a process, a specific recoding signal in the mRNA molecule causes the growing polypeptide chain occasionally to slip backward by one nucleotide on the ribosome as translation proceeds. The ribosome then resumes translation in a new reading frame resulting in production of a truncated protein. In an embodiment of the invention, a recoding signal sequence, which consists of the nucleotides UUUUUUA, may be included in AAV REP encoding recombinant helper plasmids to produce the desired low level expression of AAV REP protein.

The level of REP expression may also be controlled by altering the stability of REP mRNA. More specifically, the half life of the REP mRNA may be significantly decreased by including specific sequences known to stimulate RNA degradation in the REP gene. For example, the half-life of the REP mRNA may be significantly decreased by cloning of a sequence rich in A and U nucleotides in the 3' untranslated (UTR) of the REP gene. This AU-rich sequence accelerates mRNA degradation. In addition, REP mRNAs containing recognition sites in their 3' UTR for specific endonucleases that cleave RNA may be generated using recombinant DNA techniques. The use of such sequences will result in low level expression of AAV REP protein.

5.2. ANTISENSE AND RIBOZYME BASED REGULATION OF REP PROTEIN EXPRESSION

In another embodiment of the invention, antisense and ribozyme molecules which inhibit expression of the REP gene can also be used in accordance with the invention to reduce the level of REP gene expression, thus effectively reducing the level of REP gene activity. Still further, triple helix molecules can be utilized in reducing the level of REP gene activity. Such techniques are described below.

Antisense approaches involve the design of oligonucleotides (either DNA or RNA) that are complementary to REP gene mRNA. The antisense oligonucleotides will bind to the complementary REP gene mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non- translated, non-coding regions of REP could be used in an antisense approach to inhibit translation of REP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of REP gene mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of REP sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the REP RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the REP sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5 -methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

A preferred method of delivery utilizes a recombinant DNA construct in which the antisense oligonucleotide is placed under the control of a strong pol III or pol II promoter. The use of such a construct to transfect host cells will result in the transcription of sufficient amounts of single stranded RNAs that will form complementary base pairs with the REP gene transcripts and thereby prevent translation of the REP or pathway gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3'long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary REP RNA, followed by a endonucleolytic cleavage. The composition of ribozyme molecules must include one or more sequences complementary to the REP gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding REP gene proteins. Ribozyme molecules designed to catalytically cleave REP gene mRNA transcripts can also be used to prevent translation of REP gene mRNA and expression of REP gene. (See, e.g., PCT International Publication WO90/11364, published Oct. 4, 1990; Sarver et al., 1990, Science 247:1222–1225). While ribozymes that cleave mRNA at site specific recognition sequences can be used to destroy REP gene mRNAs, the use of hammerhead ribozymes is preferred. Hammerhead ribozymes cleave mRNAs at locations dictated by flanking regions that form complementary base pairs with the REP mRNA. The sole requirement is that the REP mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the REP mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a REP RNA sequence whereafter cleavage of the REP RNA takes place. The invention encompasses those Cech-type ribozymes which REP eight base-pair active site sequences that are present in REP or pathway gene.

As in the antisense approach, the ribozymes can be composed of modified oligonucleotides (e.g. for improved stability, targeting, etc.) and should be delivered to cells which express the REP gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous REP gene messages and inhibit translation. Because ribozymes unlike antisense molecules, are catalytic, a lower intracellular concentration is required for efficiency.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.3. CELL LINES ENGINEERED TO EXPRESS LOW LEVELS OF REP PROTEIN

Cell lines may be engineered that will natively express low levels of the AAV REP proteins. To engineer an AAV REP producing cell line, cells can be tranfected with recombinant helper plasmids vector into which the AAV REP open reading frame has been inserted. Standard recombinant DNA techniques may be used to construct the recombinant vectors using the methods described above in Section 5.1. (Ausubel, F. et al., eds., Current Protocols in Molecular Biology, Wiley & Sons, New York, 1994). Transfection may be accomplished with any of the standard techniques in the art. Alternatively, a cell line can be established with the use of viral vectors that are capable of integrating DNA into the host cell genome. Examples of these vectors include those derived from retroviruses or AAV.

Cell lines which may be chosen for integration include but are not limited to HeLa, COS, NIH 3T3, and others well known to those skilled in the art. The REP coding region may be linked to any number of heterologous promoters that can be activated in the chosen cell line. Additionally, this insertion cassette (REP genes and promoter) may be linked to a gene coding for a selectable marker, in which case the integration of the REP coding region with the linked marker will confer the particular phenotype afforded by the marker to a stably transfected cell. Thus, the cells that have successfully integrated the REP genes will be selectable. Alternatively, the selectable marker may be transfected on a separate plasmid.

Promoters to express the REP proteins within a cell line may be drawn from those that are functionally active within the host cell. Such promoters, which are well known in the art, will include those promoters that are highly regulated within the host cell resulting in low level expression of the viral REP proteins. Inducible promoters may be also be used in the practice of the invention, including but not limited to, the metallothionine promoter (MT), the mouse mammary tumor virus promoter (MMTV), and others known to those skilled in the art.

Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Stable expressing cell lines may also be constructed by linking the AAV ITR sequence to an expression cassette containing the REP coding region with the appropriate transcriptional signals to allow for integration into the host cell genome.

Detection of the expression of the REP genes can be performed by standard techniques including Northern analysis, immunoblotting, and immunoprecipitation. Such techniques may be utilized to identify cells that express low levels of REP protein.

5.4. PRODUCTION OF RECOMBINANT VIRUS STOCKS

The present invention relates to methods for efficient production of high titre stocks of rAAV through regulation of expression of the AAV REP proteins. The methods of the invention comprised culturing a eukaryotic cell containing helper virus, recombinant DNA encoding AAV CAP and REP protein, and a recombinant nucleic acid containing a DNA sequence of interest and the required cis-acting AAV terminal repeat structures.

A primary goal of the present invention is to provide methods for expressing in trans low levels of REP protein or to express REP protein with decreased biological activity and/or reduced half-life. The methods of the invention are based on the observation that reduced expression or activity of the REP protein results in production of high titre stocks of rAAV.

To generate recombinant viral stocks, the recombinant nucleic acid containing the DNA sequence of interest may be transfected into a host cell line that is capable of providing helper virus function, and supplying in trans AAV REP and CAP proteins. The REP and CAP proteins are required for replication and encapsidation of the linear recombinant nucleic acid into mature viral particles.

The REP and CAP proteins may be supplied in trans by transfection of the host cell line with a recombinant plasmid that is capable of coding for each of the proteins. DNA transfections maybe carried out using methods well known to those skilled in the art. These may include DNA transfection by lipofection, electroporation or calcium phosphate precipitation (Ausubel, et al., 1989, in Current Protocols for Molecular Biology, Green Publishing Associates, Inc. and John Wiley & Sons, Inc., New York). The plasmid is transfected into the host cell line with the intention of either transiently or stably expressing the REP and CAP proteins.

In addition to expressing the viral REP and CAP proteins, the host cell lines must be able to provide helper virus function. Both adenovirus and herpes simplex virus may serve as helper viruses for replication and encapsidation of DNA fragments containing the cis-required AAV terminal repeat sequences. Any host cell permissive for infection by either of these two viruses or any virus that acts as a helper virus for AAV, may be used in the practice of the invention. The multiplicity of infection (MOI) and the duration of the infection time will depend on the type of virus used and the cell line employed and such techniques are well known to those skilled in the art.

5.5. USES OF RECOMBINANT AAV VIRAL STOCKS

The rAAV viral stocks may be used in gene therapy for the purpose of transferring genetic information into appropriate host cells for the management and correction of human diseases including inherited and acquired disorders such as cancer and AIDS. The rAAV can be administered to a patient at therapeutically effective doses. A therapeutically effective dose refers to that amount of the compound sufficient to result in amelioration of symptoms of disease.

Toxicity and therapeutic efficacy of the rAAV can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses which exhibit large therapeutic indices are preferred. While doses that exhibit toxic side effects may be used, care should be taken to design a delivery system that targets rAAV to the site of treatment in order to minimize damage to untreated cells and reduce side effects.

The data obtained from cell culture assays and animal studies can be used in formulating a range of dosage for use in humans. The dosage of such rAAV lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions comprising the rAAV for use in accordance with the present invention, may be formulated in conventional manner using one or more physiologically acceptable carriers or excipients. For example, the rAAV may be suspended in a carrier such as PBS (phosphate buffered saline).

The rAAV and their physiologically acceptable salts and solvates may be formulated for administration by inhalation or insufflation (either through the mouth or the nose) or for oral, buccal, parenteral or rectal administration.

For administration by inhalation, the rAAV for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

The rAAV may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the rAAV may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

6. EXAMPLE

LOW LEVEL EXPRESSION OF AAV REP INCREASES THE EFFICIENCY OF RECOMBINANT VIRAL PRODUCTION

The experimental results described below demonstrate that low level expression of AAV REP proteins increases the efficiency of recombinant AAV viral production.

6.1. MATERIALS AND METHODS
6.1.1. AAV HELPER PLASMIDS CONSTRUCTION

Various AAV helper plasmids were constructed following standard protocols. AAV/AD is a previously published AAV packaging plasmid containing the entire AAV coding sequences including promoter p5 and has a MW of ~8.2 kb (Samulski et al., 1989, Cold Spring Harbor Lab. Press). Plasmid CMV/AAV also 8.2kb contains the entire AAV coding sequences except that the AAV p5 promoter was substituted by a cytomegalovirus immediate early promoter (CMV). Plasmid pSV/AAV is a construct similar to pCMV/

AAV except that an SV40 late promoter was substituted for AAV p5 promoter. This plasmid is 7.8 kb in size. Plasmid HIV/AAV also contains the entire AAV coding sequences except the AAV p5 promoter was substituted by an HIV long terminal repeat promoter. The construct was made by three fragment ligation. The first fragment was the SspI-HindIII fragment from pHIV-Rep (Antoni et al., 1991, Journal of Virology 65:396–404) containing the complete HIV promoter and portion of the Rep gene. The second fragment was the HindIII-SnaBI fragment from psub2Ol (Samulski et al., 1988, Journal of Virology 62:206–210) containing the rest of the Rep gene and the entire Cap gene along with the polyadenylation site. The third fragment was the SspI-SmaBI fragment from Bluescript KS(+) (Stratagene) containing the plasmid origin and Amp$^r$ gene. This construct is 7.6. -kb in size. Plasmid ACG-2 is a variant of AAV/AD containing an ATG to ACG mutation in the start codon of Rep [50], which reduces Rep protein synthesis, and is identical in size as the parental plasmid pAAV/Ad (8.2 kb). All the constructs were characterized by restriction analyses and some of them by sequencing. The rAAV vector plasmid pdx31-LacZ was published previously (Muzyczka, N., 1991, Seminars in Virology 2:281–290). All plasmids were purified by double CsCl density gradient ultracentrifugation for transfection experiments (Sambrook et al. 1989, Molecular Cloning: a laboratory manual. Cold Spring Harbour Press, CSH, 2nd edition).

6.1.2. VIRUSES AND CELLS rAAV vector was generated by calcium phosphate cotransfection methods as described previously (Xiao et al., 1996, J. Virol. 70:8098–8108). Briefly, human 293 cells were passed one day before transfection in DMEM (Gibco) containing 10% FBS (Gibco) with"streptomycin and penicillin. At about 80% confluence, the cells were fed with 10 ml fresh IMDM media(Gibco) containing 10% FBS without antibiotics 1 to 2 hours before transfection. Total 25 $\mu$g of plasmid DNA (vector plus helper at various ratio) was dissolved in 1 ml of 0.25 M CaCl2 and then quickly mixed with 1 ml of 2XHBS buffer (50 mM HEPES, 280 mM NaCl and 1.5 mM Na2HPO$_4$, pH 7.12). The DNA complex was slowly added to the cells. After incubation for 8 hours, the cells were fed with fresh DMEM medium (Gibco) containing 10% FBS and antibiotics, and infected with Adenovirus 5 (dl309) at 2 m.o.i. (multiplicity of infection). Transfection efficiencies were monitored by staining a duplicate plate for $\beta$ gal gene expression and counting the number of blue cells. Two day post Ad infection, the cells were harvested together with the media and 0.1 ml of 1 M Tris-Cl (pH 8.5) was added to adjust the pH of the media. Following four cycles of freeze-thaw and removal of cell debris, the rAAV viral lysate was heated at 56° C. for 30 minutes to inactivate the adenovirus and stored at −20° C. before use.

The titers of AAV-LacZ virus were determined by counting the blue cells after X-gal staining, following coinfection of 293 cells with various dilution's of the rAAV stocks and 1 m.o.i. of adenovirus dl3O9 for 24 hours. All experiments were done in triplicate to ensure reproducibility and average taken for final titer.

6.1.3. ASSAY OF rAAV DNA REPLICATION

The rAAV DNA was recovered from the transfected cells by the method of Hirt extraction (Hirt, B., 1967, J. Mol. Biol. 26:365–369) with modifications. Briefly, the cell pellet from 1/10 to 1/5 of a 10 cm dish was resuspended in 270 $\mu$l of 20 mM Tris-Cl, 20 mM EDTA(pH8.0) and lysed by addition of 30 $\mu$l of 10% SDS. The cell lysate was incubated at 37° C. for 1 hour with 50$\mu$g/ml proteinase K and mixed with 80 $\mu$l of 5 M NaCl. After stored on ice for more than 1 hour, the cell lysate was centrifuged at 15,000 rpm at 4° C. for 30 minutes. The supernatant was recovered and subsequently extracted with phenol, phenol-chloroform and chloroform. Low molecular weight DNA was precipitated with equal volume of isopropanol, rinsed with 70% ethanol specific protein bands were visualized with chemiluminescence reagent (DuPont) exposed to X-ray film.

6.2. RESULTS

6.2.1. EFFICIENT REP GENE EXPRESSION FROM HETEROLOGOUS PROMOTERS IN THE ABSENCE OF ADENOVIRUS

In order to achieve high level Rep gene expression in an adenovirus independent manner, we have constructed a number of AAV helper plasmids containing heterologous promoters substituted for the AAV p5 sequence. The heterologous promoters were the cytomegalovirus (CMV) immediate early region, HIV long terminal repeat and the SV40 late promoter (FIG. 1). These sequences are among the strongest constitutive viral promoters commonly used and should express high levels of Rep. A helper plasmid pAAV/Ad (Samulski et al., 1989, J. Virol. 63:3822–3828), which retains the endogenous p5 promoter, was included in this study as a control. To determine the effect of low level Rep expression on rAAV production, a novel plasmid pACG-2 was also constructed as described above, see Section 6.1.1. This construct is identical to pAAV/Ad except that a point mutation has converted the start codon of Rep from ATG into a less efficient ACG codon. AAV utilizes the ACG start codon for AAV Vp2 capsid production, which is expressed at low levels from the same MRNA that encodes the major capsid protein Vp3. Since this mechanism of regulation is utilized by AAV, it was expected that this point mutant would reduced Rep protein synthesis without altering AAV viral mRNA levels. The various AAV helper plasmids which carried specific promoter elements in place of the AAV p5 promoter only differed at most by 600 bp (PHIV/AAV 7.6kb)when compared to the parental plasmid p AAV/AD (8.2 kb).

Repression of AAV p5 (Labow et al., 1986, J. Virol. 60:251–258; Laughlin et al., 1982, J. Virol. 41:868–876; Pereira et al., 1997, J. Virol. In Press) and heterologous promoters such as SV40 (Labow et al., 1987, Mol. & Cell. Biology 7: 1320–1325), HIV (Antoni et al., 1991, J. Virology 65:396–404; Horer et al., 1995, J. Virol. 69:5485–5496) and CMV (Heilbronn et al., 1990, J. Virol. 64:3012–3018) by rep in the absence of ad infection was overcome by using human 293 cells. E1A gene products have been shown to transactivate AAV p5 Shi et al. 1991, Cell 67: 377–388), CW (Gorman, 1989, Virology 171:377–385) and HIV (Rice et al., 1988, Proc. Nat. Acad. Sci. 85(12):4200–4204) promoters. E1A gene products in 293 cells will counteract the repression by AAV Rep proteins, and thereby increase Rep gene expression from these various promoters in the absence of ad infection. The various AAV constructs were transfected into 293 cells with or without Ad infection, and assayed for Rep gene expression 48 hours post transfection by Western blot analysis using anti-Rep monoclonal antibody (Hunter et al., 1992, J. Virology 66:317–324). From the experimental results shown in FIG. 2, several observations can be made. First, in the absence of adenovirus in 293 cells, Rep gene expression was detected from all five AAV constructs, (FIG. 2, lane 1–5). Plasmids pCMW/AAV and pHIV/AAV expressed extremely high levels of Rep, whereas pSV/AAV and pAAV/Ad had modest expression (FIG. 2, compare lanes 3 & 4 with lanes 1 and 5). The lower expression from the SV40 promoter in 293 cells is most likely due to SV40 enhancer repression by E1A proteins as previously described (Gorman et al., 1989, Virology 171:377–385; Velcich et al., 1985, Cell. 40:705–716). As expected, plasmid pACG-2 generated the least amount of Rep (FIG. 2, lane 2). Second, in the presence of adenovirus, the levels of Rep appeared the same as the minus Ad extracts for pCMV/AAV, pHIV/AAV and pSV/AAV (compare FIG. 2, lanes 3, 4 & 5- with lanes 8,9 & 10). However, for pAAV/Ad and pACG-2, the Rep levels appeared slightly lower after Ad infection, implying further modulation of AAV gene regulation by Ad coinfection. Third, although Rep 52/40 expression was not altered after Ad infection, the ratio of Rep over Rep52/40 was significantly different among the various constructs (FIG. 2). The helper plasmids with strong heterologous promoters, such as pCMV/AAV and pHIV/AAV, demonstrated obvious abnormal Rep vs. Rep52/40 ratios (FIG. 2, lanes 3 to 5 and 8 to 10), while pAAV/Ad expressed p5 and p19 Bioducts at roughly one to one ratio (FIG. 2, lanes 1 & 6). For PACG-2, levels were less than one (FIG. 2, lanes 2 & 7), suggesting that p19 products (Rep52/40) were made at higher levels than the p5 products (Rep).

6.2.2. EXPRESSION OF REP GENE WAS NOT SUFFICIENT TO REPLICATE rAAV DNA

Since these results demonstrate that high levels of Rep protein can be expressed independent of ad infection, rAAV DNA replication was assayed under these conditions. Plasmids pCMV and PHIV, which demonstrated highest expression of Rep, were tested in cotransfection experiments with a rAAV-LacZ vector plasmid as a replication substrate (McCown et al., 1996, Brain Research 713:99–107). As a control, the same constructs were assayed for rAAV-LacZ replication in the presence of Ad infection.

48 hours post transfection, low molecular weight DNA was recovered and analyzed by Southern blot. To distinguish between input plasmid and newly replicated DNA, samples were treated with or without Dpn I endonuclease. An autoradiography of the experiment is shown in FIG. 3. Resistance to Dpn I digestion suggested that in the presence of Ad infection, Rep proteins from PCMV/AAV and PHIV/AAV successfully replicated the rAAV-LacZ vector DNA (FIG. 3, lanes 3 & 4 represent PCW/AAV and lanes 7 & 8 represent pFUV/AAV). However, sensitivity to Dpn I digestion in the absence of Aa infection (FIG. 3, lanes 1 & 2, pCNW/AAV and lanes 5 & 6, pHIV/AAV), suggested that rAAV vector DNA failed to replicate even though abundant Rep proteins were produced from these helper constructs (FIG. 2, lanes 3 & 4). Similarly, cotransfection of the rAAV-LacZ vector plasmid, with other helper plasmids, such as pAAV/Ad and PSV/AAV, in the absence of Ad infection also failed to replicate the vector DNA. These results support the conclusion that constitutive Rep gene expression is not sufficient to mediate AAV DNA replication and that other ad helper functions besides the constitutive expression of E1 in 293 cells is required.

6.2.3. OVEREXPRESSION OF REP GENE INHIBITS rAAV TITERS

The above experiments demonstrated that the new helper constructs can obtain high levels of Rep proteins which are functional for AAV replication only in the presence of Ad coinfection. To further characterize these helper constructs for rAAV production, the yield of vector particles generated after transfection experiments was measured. For example, an 1:1 ratio of rAAV vector vs. helper plasmid (pAAV/Ad) results in optimal rAAV yield when using calcium phosphate transfection method in 293 cells (Xiao et al., 1996, J. Virol. 70:8098–8108). The calcium phosphate method was used to measure the efficiency of the new helper plasmids in this experiment. Three different vector:helper ratios (3:1, 1:1 and 1:3) were tested that covered a 9 fold range. Eight hours post transfection, the media was changed and the cells were infected with Ad5 dl3O9 and incubated for additional 48 to 60 hours till full cytopathic effect (CPE) was observed. Since approximately 10% to 30% of the rAAV viruses generated are released in the culture media, the cells were harvested together with the media before assaying for particle number. After four cycles of freeze-thaw and removal of cell debris, the lysates were heated at 56° C. for 30 minutes to inactivate any residual adenovirus and tittered on 293 by staining for b-gal activity (see Section 6.1).

As shown in Table 1, helper plasmids pCMV/AAV and pHIV/AAV generated the lowest rAAV yields, even though these constructs produced the highest Rdp levels. Plasmid pSV/AAV resulted in rAAV yields higher than pCMV/AAV and pHIV/AAV but significantly lower than pAAV/Ad. This is an interesting observation since both of these plasmids produced similar level of Rep (see FIG. 2, compare lane 1 and 6 with lane 5 and 10). The overall yields of rAAV generated from pCW/AAV, pHIV/AAV and pSV/AAV were not dramatically effected by the 9 fold range of vector:helper ratio (Table 1), suggesting that the rate-limiting factor is not merely the level of rep protein or quantity of helper plasmid, but some fundamental difference between pAAV/Ad and the other three helper plasmids. As possible explanations for the decrease in vector yield, pCMV/AAV and pHIV/AAV overexpression of Rep may have inhibited other genes, both viral (AAV and/or Ad) and cellular. In addition, the substitution of the p5 promoter may have removed essential cis-acting regulatory functions required for appropriate p19 and p40 expression (McCarty et al., 1991, J. Virol. 65:2936–2945.

This hypothesis is supported by the results of helper plasmid pACG-2 which produced the highest rAAV titers (Table 1). This construct retained the p5 promoter sequences but reduced Rep expression through inefficient translational initiation (FIG. 1; FIG. 2, lanes 2 & 7). The average rAAV yields from this plasmid was increased by 8-fold when compared to its parental plasmid AAV/AD. The results suggested that unregulated overexpression of Rep may have a negative effect, while lower but sufficient Rep expression can generate higher rAAV yields.

These observations are not in agreement with a previous report (Flotte et al., 1995, Gene Therapy 2:29–37), where an AAV helper plasmid (pRS5) containing the same HIV LTR showed a 7.5 fold increase in rAAV virus yield when compared to pAAV/Ad. In the experiments described herein the helper construct pHIV/AAV gave rise to much lower rAAV yields than pAAV/Ad. One important variable which may explain this difference is the addition of adenovirus relative to transfection. In our experiments adenovirus infection was carried out 8 hours post plasmid transfection instead of 1 hour before as described by Flotte et al (Flotte et al., 1995, Gene Therapy 2:29–37). In an attempt to better explain these differences, this possibility was tested by infecting with Ad at one hour before, simultaneously, or 8 hours post plasmid transfection. The cells were harvested 48 hours after Ad infection and the rAAV titers were measured. The results shown in Table 2 indicated that when pAAV/Ad was used as the helper plasmid less than 2-fold differences in rAAV titers were observed when the time of Ad super infection was varied (Table 2). However, the addition of Ad prior to pHIV/AAV transfected plates was important (Table 2). rAAV titers were about 100 fold higher ($1.5–1.7 \times 10^7$ transducing units/10 cm plate) when Ad infection was carried out one hour before or simultaneously rather than 8 hours post transfection ($1.8 \times 10^5$ transducing units/10 cm plate) (Table 2). This implies that the presence of Ad gene expression prior to the onset of AAV Rep gene expression has a significant effect of rAAV production when using pHIV/AAV as a helper plasmid. Regardless, the best titers from pHIV/AAV were still about 10 fold lower than that of pAAV/Ad. Since pAAV/Ad contains Ad ITRs flanking AAV genes, the Ad ITR sequences may influence AAV gene expression and explain the difference in vector yield observed. To examine this possibility, the AAV gene cassette was deleted from pAAV/Ad and replaced by pHIV/AAV. This construct like pAAV/Ad now has HIV/AAV sequences flanked by the Ad ITRS. This new variant of pHIV/AAV/Ad did not produce better rAAV yields despite the addition of the Ad ITRs. The discrepancy between our results and others (Flotte et al., 1995, Gene Therapy 2:29–37) can only partially be attributed to the difference in the helper plasmids. However, based on the results observed concerning the time of addition for Ad infection with pHIV/AAV, this may be the rate limiting factor which influences rAAV yields when using strong constitutive promoters such as the HIV LTR. In addition, one may need to consider the numerous variables utilized during rAAV production, such as different lots of 293 cells, Ad strain, various transfection and infection methods, in order to make direct comparisons.

6.2.4. OVEREXPRESSION OF REP GENE INHIBITED rAAV DNA REPLICATION AND CAP GENE EXPRESSION

To explore why overexpression of Rep resulted in lower rAAV particles, two essential steps were examined, viral DNA replication and capsid protein synthesis. To examine rAAV replication, the rAAV-LacZ plasmid was cotransfected with various AAV helper plasmids followed by adenovirus infection. At 24 and 48 hours post transfection, low molecular weight DNA was isolated and DpnI digested, followed by Southern analysis using 32p labeled LacZ probe. The experimental result indicated that rAAV DNA replication was significantly lower when pCMV/AAV (FIG. 4, lanes 1 & 2) and pHIV/AAV (FIG. 4, lanes 3 & 4) where used as helper plasmids, as compared to pSV/AAV, pAAV/Ad and pACG-2 (FIG. 4, lanes S through 10). PhosphoImager quantitation of the monomer bands at the 48-hour time point revealed approximately 80% reduction in vector DNA replication when comparing pCMV/AAV and PHIV/AAV to pAAV/Ad. On the other hand, no significant difference was found between pSV/AAV, pAAV/Ad and pACG-2 (FIG. 4, lanes 5 through 10 and data not shown). Interestingly, rAAV DNA replication was not reduced in pACG-2 transfected cells, although the Rep level were considerably lower (FIG. 2, lane 7). Since pCMV/AAV and pHIV/AAV expressed highest levels of Rep (FIG. 2, lanes 8 & 9) which resulted in lowest levels of rAAV DNA replication (FIG. 4, lanes 1 through 4), these data suggest that Rep are not rate-limiting factors, but may instead interfere with the vector DNA replication when overexpressed. The mechanism of inhibition remains unknown.

Since capsid proteins are essential for particle formation, the accumulation of these proteins from the various helper plasmids was also examined. 48 hour post transfection, cells were harvested and analyzed by Western blot using an anti-capsid polyclonal antibody. The results are shown in FIG. 5. In the absence of Ad infection, all helper plasmids generated low but detectable level of capsid proteins, consistent with published observations that Ad infection enhances AAV capsid gene expression (Muzyczka, N., 1992, Current Topics in Microbiology & Immunology 158:97–129). In the presence of adenovirus infection, pACG-2 transfected cells synthesized and/or accumulated the highest level of capsid proteins (FIG. 5, lane 5) while pCMV/AAV and pHIV/AAV produced the lowest (FIG. 5, lanes 1 & 2). From these results, a negative correlation was observed between high Rep levels (FIG. 2, pCMV/AAV lanes 8 and pHIV/AAV lane 9) and efficient capsid gene expression (FIG. 5, pCMV/AAV lanes 1 and pHIV/AAV lane 2). For pACG-2, just the reverse was observed, low rep expression (FIG. 2, lane 7) resulted in highest capsid gene expression (FIG. 5, lane 5). While pSV/AAV replicated rAAV DNA to similar levels as pAAV/AD and pACG-2 (see FIG. 4 lanes 5–10), and expressed AAV capsid gene products higher than pCMV/AAV and pHIV/AAV (FIG. 5, compare lane 3 to 1 and 2), these capsid gene products were reduced when compared to helper plasmids pAAV/Ad, and pACG-2 (FIG. 5, lane 3 vs 4 and 5). From this analysis, a direct correlation can be made between the amount of Rep protein produced, level of AAV capsid expression (FIG. 5) and the yield of rAAV (table 1) with pACG-2 expressing the lowest levels of Rep, the highest amounts of capsid protein and the best yields of rAAV followed by pAAV/AD, pSV/AAV, pHIV/AAV and pCMV/AAV.

TABLE 1

Comparison of rAAV titers by different helper plasmids

| Helper plasmid | Vector/helper ratio | rAAV titer TU/ptate[a] | TU/cell[b] |
|---|---|---|---|
| CMV/AAV | 3:1 | $2.0 \times 10^5$ | 0.04 |
|  | 1:1 | $8.5 \times 10^4$ | 0.02 |
|  | 1:3 | $8.5 \times 10^4$ | 0.02 |
| HIV/AAV | 3:1 | $1.4 \times 10^5$ | 0.03 |
|  | 1:1 | $8.5 \times 10^4$ | 0.02 |
|  | 1:3 | $1.2 \times 10^5$ | 0.02 |
| SV/AAV | 3:1 | $8.3 \times 10^6$ | 1.6 |
|  | 1:1 | $6.0 \times 10^6$ | 1.2 |
|  | 1:3 | $5.5 \times 10^6$ | 1.1 |
| AAV/Ad | 3:1 | $8.5 \times 10^7$ | 17 |
|  | 1:1 | $1.4 \times 10^8$ | 28 |
|  | 1:3 | $1.0 \times 10^8$ | 20 |
| ACG-2 | 3:1 | $5.0 \times 10^8$ | 100 |
|  | 1:1 | $1.1 \times 10^9$ | 220 |
|  | 1:3 | $8.0 \times 10^8$ | 160 |

[a]The rAAV-LacZ yields were mean values from three experiments performed with a 10-cm plate of human 293 cells. The transducing units (TU) were determined by infecting 293 cells with Ad at an MOI of 1 and various ditutions of heat-inactivated rAAV virus stocks. After X-Gal staining, each blue cell was translated into 1 TU.
[b]The number of transducing units (TU) produced per cell was obtained by dividing the titers (total TU) from each 10-cm plate by the total number of 293 cells (approximately $5 \times 10^6$).

TABLE 2

Effects of Ad infection time on rAAV yields

| Time of Ad infection[a] | rAAV titer (TU)[b] for: | |
|---|---|---|
|  | AAV/Ad | HIV/AAV |
| Before | $1.7 \times 10^8$ | $1.5 \times 10^7$ |
| Same | $2.5 \times 10^8$ | $1.7 \times 10^7$ |
| After | $1.9 \times 10^8$ | $1.8 \times 10^5$ |

[a]Ad infection was carried out at three different time points, 1 h before, simultaneously with, and or 8 h after DNA transfection, for the three individual samples of a given helper plasmid.
[b]The rAAV-LacZ yields were obtained from a 10-cm plate of 293 cells. The transducing units (TU) were determined by infecting 293 cells with Ad at an MOI of 1 and various dilutions of heat-inactivated rAAV virus stocks. After X-Gal staining, each blue cell was translated into 1 TU.

The present invention is not to be limited in scope by the specific embodiments described which are intended as single illustrations of individual aspects of the invention, and functionally equivalent methods and components are within the scope of the invention. Indeed, various modifications of the invention, in addition to those shown and descried herein will become apparent to those skilled in the art from the foregoing descriptions and accompanying drawings. Such modifications are intended to fall within the scope of the appended claims.

All publications and patent applications mentioned in the specification are herein incorporated by reference to the same extent as if each individual publication or patent application was specifically and individually indicated to be incorporated by reference.

What is claimed:

1. A method for producing a stock of recombinant adeno-associated virus (AAV) comprising:
    (a) co-transfecting cells permissive for adeno-associated virus replication with
        (i) a recombinant adeno-associated virus vector which contains a foreign DNA sequence and which can be incorporated into an infectious AAV virion; and
        (ii) a recombinant helper virus DNA which provides viral functions sufficient for replication and packaging into infectious virions of said recombinant adeno-associated virus vector, wherein an AAV REP 78 or REP 68 protein is expressed under regulatory control of an AAV promoter, and wherein a decreased level of REP 78 or REP 68 protein is expressed relative to the level of REP 78 or REP 68 protein expressed by a host cell that expresses wild-type REP 78 or REP 68 protein under regulatory control of an AAV REP 78 or REP 68 promoter; and
    (b) collecting virions produced.

2. The method of claim 1, wherein said recombinant helper virus DNA is a plasmid which comprises an AAV REP 78 or REP 68 promoter.

3. The method of claim 1 wherein the level of REP 78 or REP 68 protein is reduced by regulating the translation of the REP gene.

4. The method of claim 1, wherein said recombinant helper virus DNA is a plasmid which comprises an AAV p5 promoter.

5. The method of claim 1, wherein said recombinant helper virus DNA comprises a modified REP coding sequence having a mutation in the translational start codon.

6. The method of claim 5, wherein the translational start codon has been modified from ATG to ACG.

7. A host cell for producing a stock of recombinant adeno-associated virus containing a recombinant DNA vector wherein an AAV REP 78 or REP 68 protein is expressed under regulatory control of an AAV promoter, and wherein a decreased level of REP 78 or REP 68 protein is expressed relative to the level of REP 78 or REP 68 protein expressed by a host cell that expresses wild-type REP 78 or REP 68 protein under regulatory control of an AAV REP 78 or REP 68 promoter.

8. The host cell of claim 7 wherein the host cell is transiently transfected.

9. The host cell of claim 7 wherein the host cell is stably transfected.

10. The host cell of claim 7 wherein the level of REP 78 or REP 68 protein is regulated at the translational level.

11. The host cell of claim 7, wherein said recombinant helper virus DNA is a plasmid which comprises an AAV p5 promoter.

12. The host cell of claim 7, wherein said recombinant helper virus DNA is a plasmid which comprises a modified REP coding sequence having a mutation in the translational start codon.

13. The host cell of claim 12, wherein the translational start codon has been modified from ATG to ACG.

14. The host cell of claim 7, wherein said recombinant helper virus DNA is a plasmid which comprises an AAV REP 78 or REP 68 promoter.

* * * * *